United States Patent
Oh et al.

(10) Patent No.: US 6,808,909 B2
(45) Date of Patent: Oct. 26, 2004

(54) THERMOSTABLE PHYTASE WITH 2.1 Å ... CRYSTAL STRUCTURE

(75) Inventors: Tae Kwang Oh, Daejeon (KR); Nam Chul Ha, Kwangju (KR); Byung Ha Oh, Pohang (KR)

(73) Assignees: Korea Research Institute of Bioscience and Biotechnology, Daejeon (KR); Daesung Microbiological Labs. Co., Kyungki-do (KR)

( * ) Notice: Subject to any disclaimer, the term of this patent is extended or adjusted under 35 U.S.C. 154(b) by 0 days.

(21) Appl. No.: 10/043,623

(22) Filed: Jan. 9, 2002

(65) Prior Publication Data

US 2002/0142433 A1 Oct. 3, 2002

Related U.S. Application Data

(63) Continuation of application No. PCT/KR00/00002, filed on Jan. 4, 2000.

(51) Int. Cl.$^7$ .............................. C12N 9/00; C12N 9/14
(52) U.S. Cl. ....................................... 435/183; 435/195
(58) Field of Search .................................. 435/183, 195

(56) References Cited

U.S. PATENT DOCUMENTS 5,955,310 A * 9/1999 Widner et al.

6,117,433 A * 9/2000 Edens et al.

FOREIGN PATENT DOCUMENTS

WO    WO 98/06856    * 2/1998

OTHER PUBLICATIONS

Ha et al., Acta. Cryst., 1996, D55, 691–693.*

* cited by examiner

Primary Examiner—Michael Meller
(74) Attorney, Agent, or Firm—Jones Day

(57) ABSTRACT

The present invention relates to a thermostable enzyme with a 2.1 Å crystal structure of a propeller type comprising six external blades that encompass the outer boundary of the crystal and six internal calcium-binding sites that are embedded inside the above crystal. Each of the six blades comprises 4 or 5 anti-parallel β-strands, and the six calcium binding sites consist of 3 high-affinity calcium binding sites and 3 low-affinity binding sites, which are involved in the enzyme's thermostability and catalytic activity, respectively. The above-mentioned $Ca^{2+}$ binding motifs are expected to be utilized in synthesizing highly thermostable proteins and the elucidation of active sites of an enzyme from a three-dimensional structure can help to design new enzymes having those sites with the aid of recent advanced technology of protein engineering.

8 Claims, 4 Drawing Sheets

[Fig. 1]
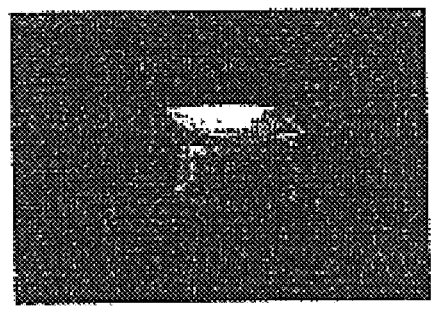
[Fig.2]
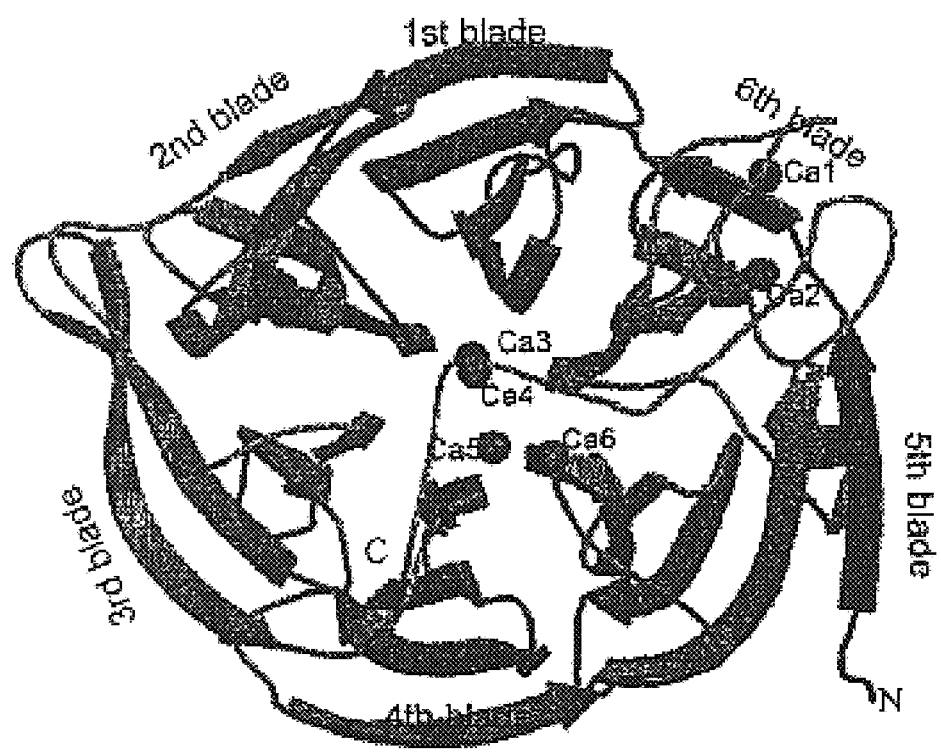

[Fig.3]
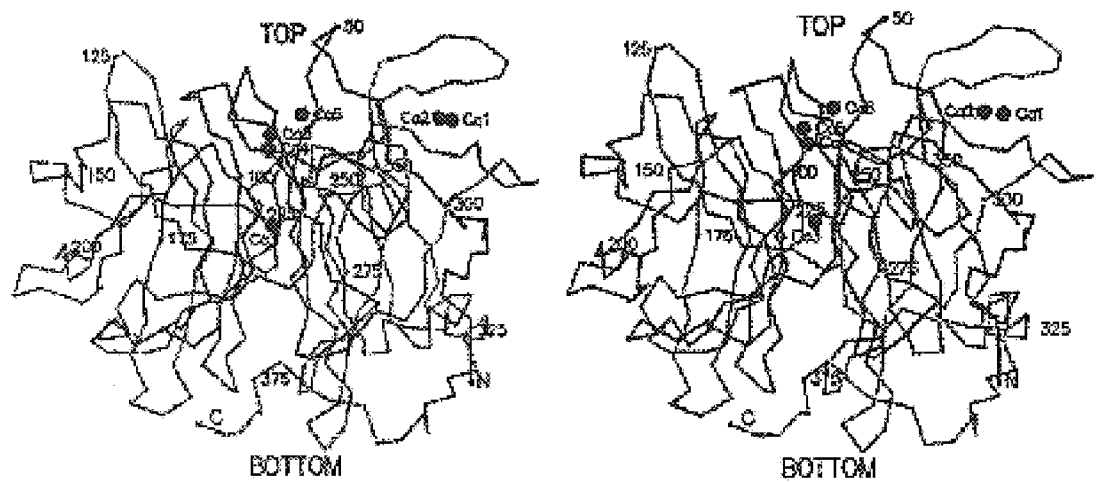
[Fig.4]
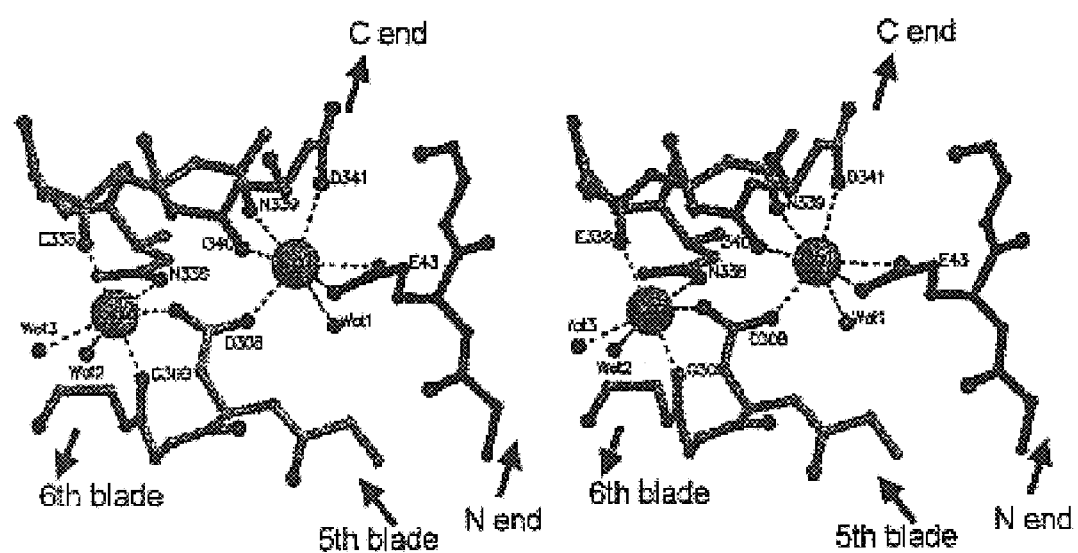

[Fig. 5]
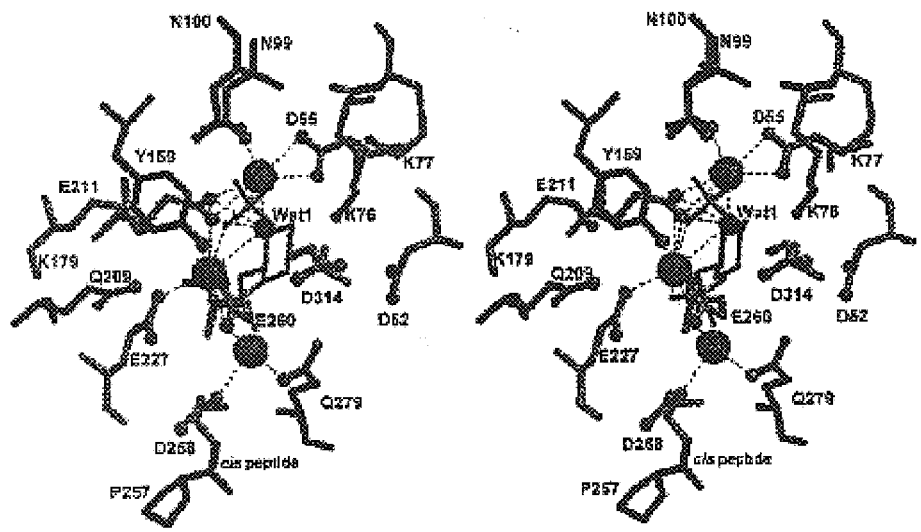
[Fig. 6]
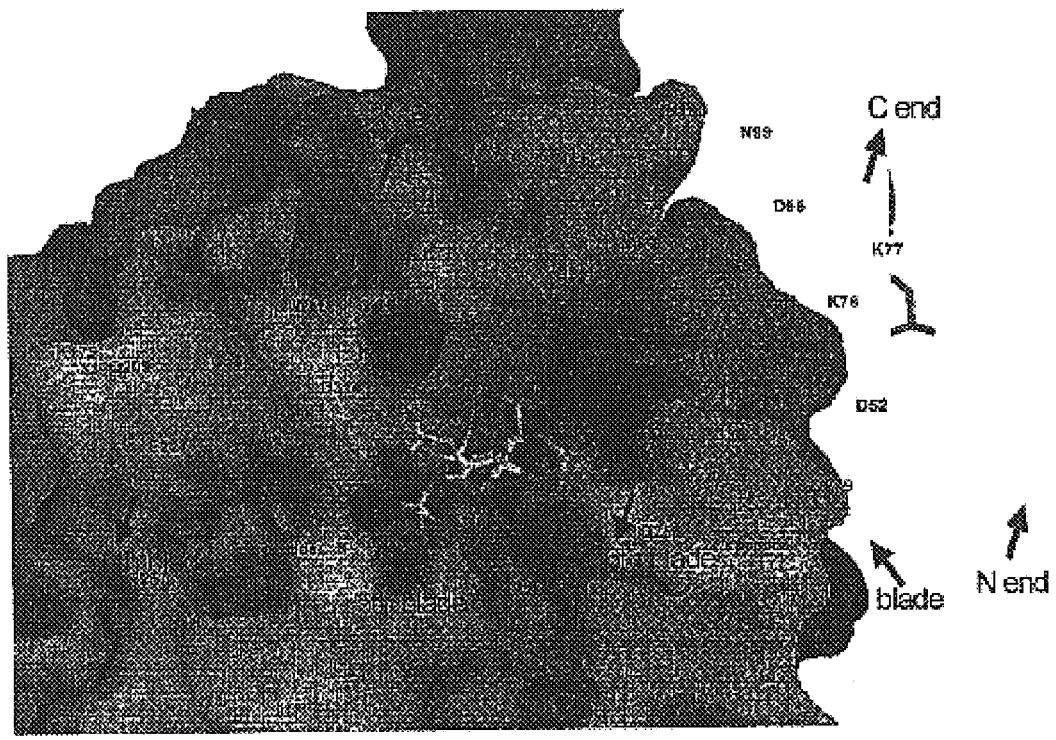

[Fig. 7]
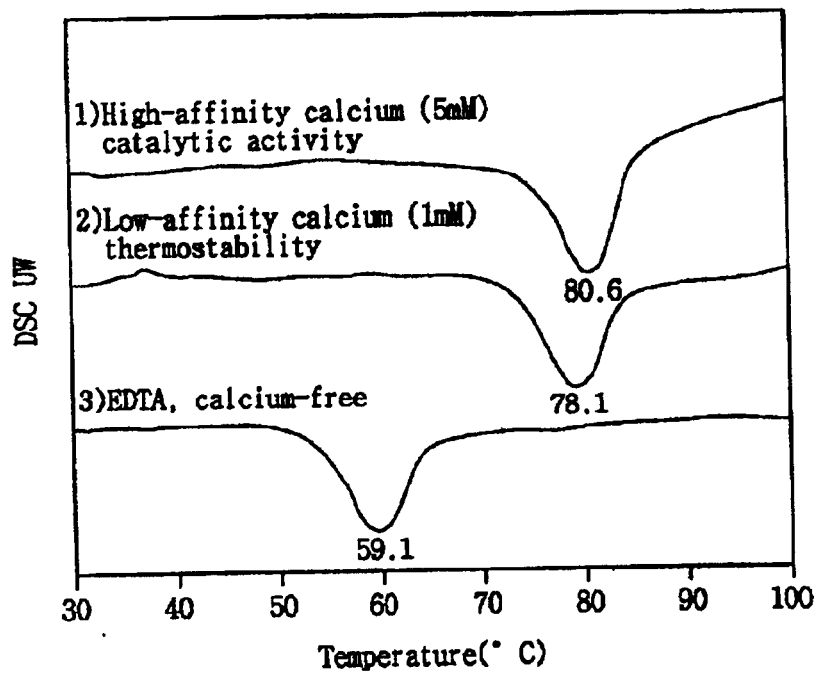
[Fig. 8]
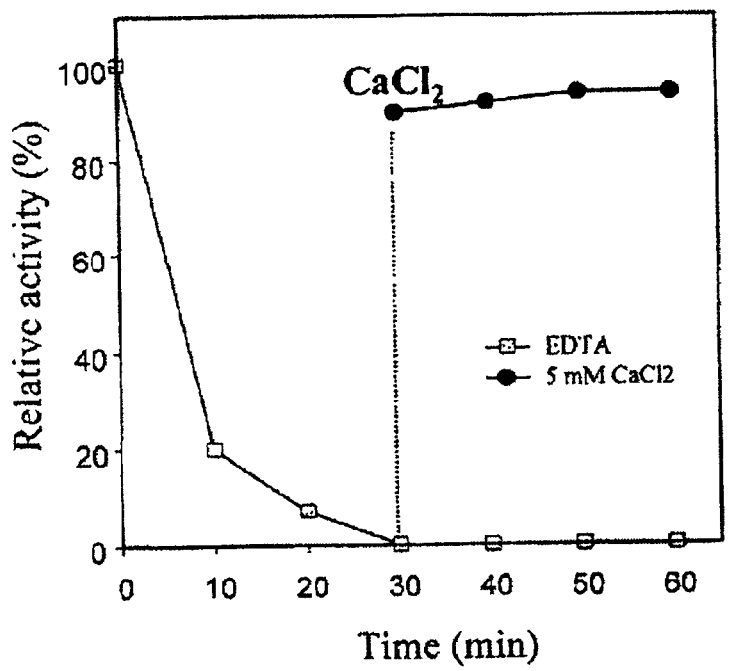

THERMOSTABLE PHYTASE WITH 2.1 Å CRYSTAL STRUCTURE

RELATED APPLICATION

This is a Continuation under 35 U.S.C. §120 of the U.S. National Stage Designation of international application no. PCT/KR00/00002, filed Jan. 4, 2000.

FIELD OF THE INVENTION

The present invention relates to a thermostable enzyme with a three-dimensional crystal structure, and more particularly to a thermostable phytase with a 2.1 Å crystal structure comprising six external blades and six internal calcium binding sites, wherein each blade consists of 4 or 5 anti-parallel β-strands.

BACKGROUND OF THE INVENTION

Phytase is an enzyme that degrades phytic acid into phosphate, phosphate inositol and inositol. The phytase, a thermostable enzyme, is known to be effective in digestion and its long-lasting catalytic activity makes the enzyme very useful as an additive for a livestock feed.

Phytic acid takes approximately 50–70 weight % of the total phosphorous stored in grain used as livestock feeds; however, monogastric animals such as hens and pigs are hardly able to utilize plant phosphate due to the deficiency in phytase in their bodies and thus most of the phytic acid they intake through the feed becomes excreted without being digested and eventually flowed into a drinking water source thus resulting in serious environmental contamination. In addition, phytic acid can bind to other essential elements of animal body such as trace minerals (e.g., Ca, Mg, Mn, Zn and Fe), amino acids and vitamins, and those nutrients bound to the phytic acid are in turn excreted in the form of an insoluble phytate without being absorbed into the body; this would not only cause the loss of nutrients required by the animal body but also bring about the devastation of natural environment. Therefore, by providing livestock with a phytase-added feed we can expect the economic benefits by reducing the amount of inorganic phosphate in feeds, the improvement of the bioavailability of the trace amount of essential bioactive materials present in livestock, and the environmental protection from contamination due to the reduction of phosphate excreted by livestock.

Despite the importance of utilization of phytase in livestock, the production of an idealistic phytase has not been very successful. First, the phytases developed so far can degrade only a few of the six phosphates in a phytic acid into phosphorous and also the production of a phytase is not economical because the enzyme requires a long period of culturing time. Moreover, since the enzyme is not very compatible with the digestive physiology of livestock, the enzyme often loses its activity in the digestive tract when fed to livestock and thus its initial purpose serving as a phosphate degrader has been much limited.

In general, a phytase is known digested in gastric tracts and then the digested phosphate is subsequently absorbed in small intestine. Therefore, it has been strongly required for the phytase to have an anti-acid property to maintain its vital enzyme activity in the presence of a strong digestive enzyme secreted in the small intestine of livestock and also a neutral type phytase, which is known to be catalytically active in small intestine, is preferred in this respect. Moreover, considering that the pelleting is performed at high temperature when feeding livestock, a thermostable phytase is a prerequisite.

A various lines of intensive global studies about a phytase have been conducted guided mostly by the studies in Europe (A. H. J. Ullah et al., J. Agric. Food Chem. 42, 423–425 (1994); K. C. Ehrlich et al., Biochem. Biophys. Res. Commun. 195, 53–57 (1993); C. S. Piddington et al, Gene, 133, 55–62 (1993)). For example, there have been studies on the effects of a phytase on animals (L. G. Young et al., J. Anim. Sci., 71, 2147–250. (1993); X. G. Lei et al., J. Anim. Sci., 72, 139–143(1994); Z. Mroz et al., J. Anim. Sci., 72, 139–143 (1994)), the structure of the phytase (D. Kostrewa et al., Nat. Struct. Biol. 4, 185–90 (1997), and a different line of study (L. F. Johnson et al., Ann. NY Acad. Sci. 165, 526–532 (1969) has recently shown that a phytase derived from *Aspergillus niger* degrades a 3' phytate prior to degrading any phosphate located in other positions.

The inventors of the present invention developed a novel phytase derived from *B. amyloliquefaciens* DS-11 that enables to degrade phytate regardless of the positions of phosphate groups in a phytate, which was found to be more suitable to the digestive physiology of livestock and also capable of maintaining its enzyme activity during the feed production when a high temperature is applied.

The novel phytase was deposited to the Genetic Engineering Center attached to Korea Research Institute of Bioscience and Biotechnology (KRIBB) and was assigned a depository number 'KCTC 0231BP'. The inventors also filed applications with the same enzyme in PCT (PCT/KR 98/00056), U.S. Pat. No. (09/142,621), Canada (2,249,014), Japan (JP9-532479) and in Korea (97-10948).

Nevertheless, the recent identification of the three-dimensional crystal structure of a phytase can help us to initiate further researches on developing new version of a phytase with an improved thermostability and an increased enzyme activity.

SUMMARY OF THE INVENTION

The present invention relates to a thermostable phytase with a 2.1 Å crystal structure of a propeller shape comprising six blades and six internal $Ca^{2+}$ binding sites. The six blades, each of which comprises 4 or 5 anti-parallel β-strands, encompass the external structure of the above crystal while the six $Ca^{2+}$ binding sites, 3 with high-affinity and the other 3 with low-affinity, are embedded internally. In addition, the above-mentioned $Ca^{2+}$ binding motifs can be applied in synthesizing highly thermostable proteins and active sites identified by the elucidation of an enzyme's three-dimensional crystal structure can help to design new enzymes having those active sites by employing the recent advanced technology of protein engineering.

BRIEF DESCRIPTION OF THE DRAWINGS

1. FIG. 1 is an X-ray crystal of a recombinant phytase.

2. FIG. 2 is a three-dimensional structure of a phytase derived from *B. amyloliquefaciens* DS-11.

3. FIG. 3 is an active site cleft of a three-dimensional structure of a phytase derived from *B. amyloliquefaciens* DS-11.

4. FIG. 4 shows high-affinity calcium binding sites in a three-dimensional structure of a phytase derived from *B. amyloliquefaciens* DS-11.

5. FIG. 5 shows low-affinity calcium binding sites in a three-dimensional structure of a phytase derived from *B. amyloliquefaciens* DS-11.

6. FIG. 6 shows putative substrate binding sites in a three-dimensional structure of a phytase derived from *B. amyloliquefaciens* DS-11.

7. FIG. 7 is a graph that shows the relationship between calcium ions and thermostability in a three-dimensional structure of a phytase derived from *B. amyloliquefaciens* DS-11.

8. FIG. 8 is a graph that shows the relationship between low-affinity calcium ions and the enzyme activity in a three-dimensional structure of a phytase derived from *B. amyloliquefaciens* DS-11.

DETAILED DESCRIPTION OF THE INVENTION

The object of the present invention is to develop a thermostable enzyme with an improved thermostability and enzyme activity comprising six external blades and six internal calcium-binding sites.

More specifically, the present invention relates to a thermostable enzyme with a propeller shape comprising six external blades and six internal $Ca^{2+}$ binding sites which are embedded inside of said six external blades, wherein said six blades are characterized in that each of which comprises 4 or 5 anti-parallel β-strands, while the six $Ca^{2+}$ binding sites are characterized in that three have high-affinity and the other three have low-affinity for calcium, respectively.

The present invention can be described in more detail as set forth hereunder.

First, one example of the enzyme having a crystal structure as mentioned in the above is a phytase. A phytase is well characterized by having a structure of six blades in the form of a propeller with the fourth strand of each blade connected to the upper part of the first strand of the next blade and each blade comprises 4 or 5 anti-parallel β-strands. Further, there are six internal calcium-binding sites embedded inside of said external blades, wherein three of them are high affinity calcium-binding sites and the other three are low affinity calcium-binding sites.

The three high affinity calcium-binding sites are characterized in that two calcium ions are located in the center of 'double clasp' near to the sixth blade, and Ca1 and Ca2 establish a bi-calcium center at Asp308 carboxylate, which serves as a bridging arm. This then strengthens the 'double clasp' by static interaction and makes the propeller structure with annular arrangement more stabilized. On the other hand, Ca3 interacts with Asp56 carboxylate and stabilizes the internal structure of a phytase and thus further strengthens heat resistant property of a phytase.

There are three low affinity calcium-binding sites in a phytase. Ca4 forms a coordinate bond with a carboxylate group of Asp55 and Glu211, and with a side chain oxygen atom of Asn99 and Asn100, and interacts with water molecule. Ca5 forms a coordinate bond with a carboxylate group of Glu227, and with a hydroxyl group of Tyr159, and also forms a coordinate bond by sharing a carboxylate group and water molecule with said Ca4. Ca6 forms a coordinate bond with a carboxylate group of Asp258, Glu260 and Gln279, and water molecule interacts with Glu211 and Asp314. That is, the bonds of Ca4, Ca5 and Ca6 not only convert side chains of a protein from a disordered state to an ordered state but also convert highly negative active sites to hydrophobic active sites thus being advantageous in bonding to a phytase and improving catalytic activity of an enzyme.

In the fifth blade, the N-terminal segment, which is an extra β-strand, is connected to the C-terminal segment by forming a (1+3) combination with the C-terminal segment and thus stabilizes the annular arrangement of β-strand.

The above results on calcium-binding motifs and active sites of an enzyme can be applied to protein engineering technology to develop enzymes which have an improved thermal stability as well as excellent catalytic activity.

The following examples illustrate various aspects of the present invention herein but are not to be construed to limit claims in any manner whatsoever.

EXAMPLE 1

The Isolation and Production of a Novel Phytase Derived from *B. amyloliquefaciens* DS-11

*Bacillus subtilis* DB104/pJPK, a recombinant plasmid harvoring pJPK, was cultured on LB medium containing kanamycin (12 μg/ml) for 20 hrs and centrifuged to recover the supernatant. The supernatant was then precipitated by 50% acetone (v/v). The precipitates was solubilized in 20 mM Tris/HCl, pH 7.0 and then soluble enzyme was heat-treated for 5 min at 70° C. in the presence of 20 mM $CaCl_2$. Phytase was purified by Superdex 200HR gel permeation chromatography with a purity of 99% or above. In addition, the 'Handing-Drop Vapor-Diffusion' method was employed to detect the initial crystal of a phytase (40 mg/ml) by using 24-well Linbro plates. The optimal crystal of a phytase was obtained from a 0.1M MES buffer (pH 6.5) at 4° C. containing 20% 2-methyl-2,4-pentandiol and it was identified as a unit cell (a=50.4, b=64.1, c=104.2 Å). Moreover, a high resolution data of a 2.1 Å phytase molecule, an asymmetric unit consisting of $P2_12_12_1$ space group, was also acquired and is shown in FIG. 1.

EXAMPLE 2

The Three-Dimensional Structure of a Phytase Derived from *B. amyloliquefaciens* DS-11

The phytase derived from *B. amyloliquefaciens* DS-11 had a three-dimensional structure of a six-bladed propeller. The high-affinity calcium binding sites and the low-affinity calcium binding sites associated with the enzyme's thermostability and catalytic activity, respectively, are shown in FIG. 2. The cleft, wherein the low-affinity calcium binding sites reside and represents the active sites of the phytase, is shown on the top portion of the three-dimensional structure as shown in FIG. 3.

As shown in FIGS. 2 and 3, the three-dimensional structure of a phytase derived from *B. amyloliquefaciens* DS-11 in the present invention is in the form of a propeller with six blades consisting of anti-parallel β-strands that connect between neighboring blades. Here, the interconnecting system among the six blades is found that the fourth β-strand of each blade is connected across the top of the molecule to the first strand of the next blade. The six blades are aligned along the shaft of the propeller-like structure. Further, the above structure is in the form of "double clasp" that can stabilize the entire structure of a phytase due to the presence of both "1+3 combination" at C-terminal and the formation of "an extra β-strand" generated by the connection of N-terminal segment to the $5^{th}$ blade. The cleft, which is thought to be the active sites of a phytase, is positioned on the upper part and the other end, the lower part, has a flat structure.

EXPERIMENTAL EXAMPLE 1

High-Affinity Calcium Binding Sites of a Phytase Derived from *B. amyloliquefaciens* DS-11

The high-affinity calcium binding sites of a phytase derived from *B. amyloliquefaciens* DS-11 were identified by Multiple Isomorphous Replacement (MIR) with 'anomalous scattering' (AS). The initial phytase was crystallized from heavy metal derivatives. As a result, 3 calcium binding sites were identified and the result is shown in FIG. 4. As shown in FIG. 4., two calcium ions are located at the center of the "double clasp" which is adjacent to the six$^{th}$ blade, and a 'bi-calcium center' is formed by Ca1 and Ca2 in Asp308 which works as a bridging arm. The two calcium ions help to strengthen the 'double clasp' and more stabilize the propeller-like structure of the enzyme by electrostatic interactions, whereas Ca3 reacts with Asp56 carboxylate to stabilize the internal structure and subsequently fortifying the thermostability of the enzyme.

EXPERIMENTAL EXAMPLE 2
Low-Affinity Calcium Binding Sites of a Phytase Derived from *B. amyloliquefaciens* DS-11

The active sites of the phytase derived from *B. amyloliquefaciens* DS-11 are located at one end of the enzyme molecule where there are a number of loops in between β-strands, and there is also a cleft consisting of negative side chains. Calcium ions are required for the full activation of the phytase. Crystals having another 3 different calcium binding sites were obtained by using the method employed in Experimental Example 1 under the condition for the crystallization including 4 mM CaCl$_2$ to detect the binding sites of those calcium ions and the result is shown in FIG. 5.

In FIG. 5, three different calcium ions form a triadic calcium center with the distance of 5.2 Å between the central Ca5 and Ca4 and 4.1 Å between the Ca5 and Ca6. Ca4 forms a coordination bond with carboxylate groups of Asp55 and Glu211, side chain atoms of Asn99 and Asn100, and also interact with a water molecule (Wat1). Ca5 forms a coordination bond with a carboxylate group of Glu227 and Glu211, a hydroxyl group of Tyr159, and also shares a carboxylate group of Glu211 and a water molecule with Ca4 to have a coordination bond. Ca6 also forms a coordination bond with carboxylate groups of Asp258, Glu260, and Gln279, and the water molecule interacts with Glu211 and Asp314. The binding among Ca4, Ca5 and Ca6 results in the transition of protein side chains from a random state into an orderly state. Moreover, the above binding among calcium ions can transform highly negative active sites of the enzyme into the active sites with hydrophobicity which eases the binding with the phytate, a substrate, and thus exhibit the activity of the enzyme.

EXPERIMENTAL EXAMPLE 3
Putative Substrate Binding Sites of a Phytase Derived from *B. amyloliquefaciens* DS-11

The activities of the phytase derived from *B. amyloliquefaciens* DS11 were measured on its 2 mM substrates of myo-inositol, hexaphosphate, mio-inositol 1-monophosphate, mio-inositol 2-monophosphate, myo-inositol 4-monophosphate, after incubating at 37° C. for 15 min in a 20 mM Tris/HCl (pH7.0) buffer. The result showed that the phytase had activities of 27%, 28% and 40% at locations 1, 2 and 4, respectively, as shown in Table 1. The FIG. 6 shows that the phytate, an electrostatic anion, is able to bind amino acids having electostatic cations such as Lys76, Lys77 and lys179.

TABLE 1

| Substrate | Relative Enzyme Activity (%) |
|---|---|
| Phytate | 100 |
| 4'-monophosphoinositol | 40 |
| 2'-monophosphoinositol | 28 |
| 1'-monophosphoinositol | 27 |

As shown in Table 1 and FIG. 6, calcium ions that bind active sites of the enzyme undergo an environmental transition, along with Lys76, Lys77 and Lys179 which are adjacent to active sites, into an electrostatic state so that the phytate, a substrate, can easily bind. The phosphate group of the phosphase bind in between Ca4 and Ca5, and neighboring phosphate groups can bind in between Ca5 and Ca6 without an electrostatic repulsion or a steric crash. In this substrate-binding mode, three residual groups of lysine can bind three other phosphate groups. In addition, the structure of a phytase derived from *B. amyloliquefaciens* DS 11 revealed that calcium ions Ca4 and Ca5 has a coordination bond with a water molecule (Wat1) and the water molecule degrade the phytase by directly attacking the phosphate group of the enzyme. Finally, the exposed active sites of the enzyme and the phytate-binding model show that the enzyme can degrade all six phosphate groups of the phytase.

EXPERIMENTAL EXAMPLE 4

The Effect of Calcium on the Thermostability of a Phytase

The effect of calcium ions on the thermostability of the phytase derived from *B. amyloliquefaciens* DS-11 was determined by using a differential scanning calorimetry. 1 mM CaCl2, 2 mM EDTA, and 5 mM CaCl2 were added to each 5% (w/v) phytase sample, respectively and the results are shown in FIGS. 7 and 8. The results showed that the addition of EDTA resulted in the removal of calcium ions from the phytase derived from *B. amyloliquefaciens* DS-11, and the Tm of the phytase also drastically decreased from 78.1° C. to 59.1° C. thus implying that the high-affinity calcium binding sites of the phytase play a crucial role in the thermostability of the enzyme. The addition of 5 mM calcium ions exhibits a state that three different calcium ions are bound to the low-affinity calcium binding sites of the phytase. The above calcium binding increased the Tm of the phytase by approximately 2.1° C. and the result indicates that the low-affinity calcium binding sites are deeply involved in the enzyme's activity. Consequently, calcium ions bound to the high-affinity calcium binding sites are involved in the thermostability of the propeller structure that contains 53% of loops, whereas those bound to the low-affinity calcium binding sites are involved in the catalytic activity of the enzyme.

What is claimed is:

1. A crystalline phytase crystallized from phytase isolated from *Bacillus amyloliquefaciens* DS 11, wherein the crystalline phytase has a structure comprising 2.1 Å crystal structure comprising six external blades and six internal calcium binding sites wherein each blade consists of four of five anti-parallel beta-strands.

2. The crystalline phytase of claim 1, which is formed using 0.1 M MES (pH=6.5) containing 5 mM calcium and 20% 2-methyl-2,4-pentadiol at 4° C.

3. The crystalline phytase of claim 1, wherein the calcium binding sites consist of three high-affinity and three low-affinity calcium binding sites.

4. The crystalline phytase of claim 3, wherein the blades are arranged in a form of a propeller, with the fourth strand of each blade connected to the upper part of the first strand of the adjacent blade.

5. The crystalline phytase of claim 4, wherein the N-terminal segment is connected to the fifth blade.

6. The crystalline phytase of claim 5, wherein the N-terminal segment forms a (1+3) combination with the C-terminal segment.

7. The crystalline phytase of claim 1, which is crystallized in a $P2_12_12_1$ space group.

8. The crystalline phytase of claim 1, wherein said phytase is thermostable.

* * * * *